May 12, 1953 W. H. ELLER Plant Pat. 1,184
PEAR TREE
Filed Oct. 18, 1949
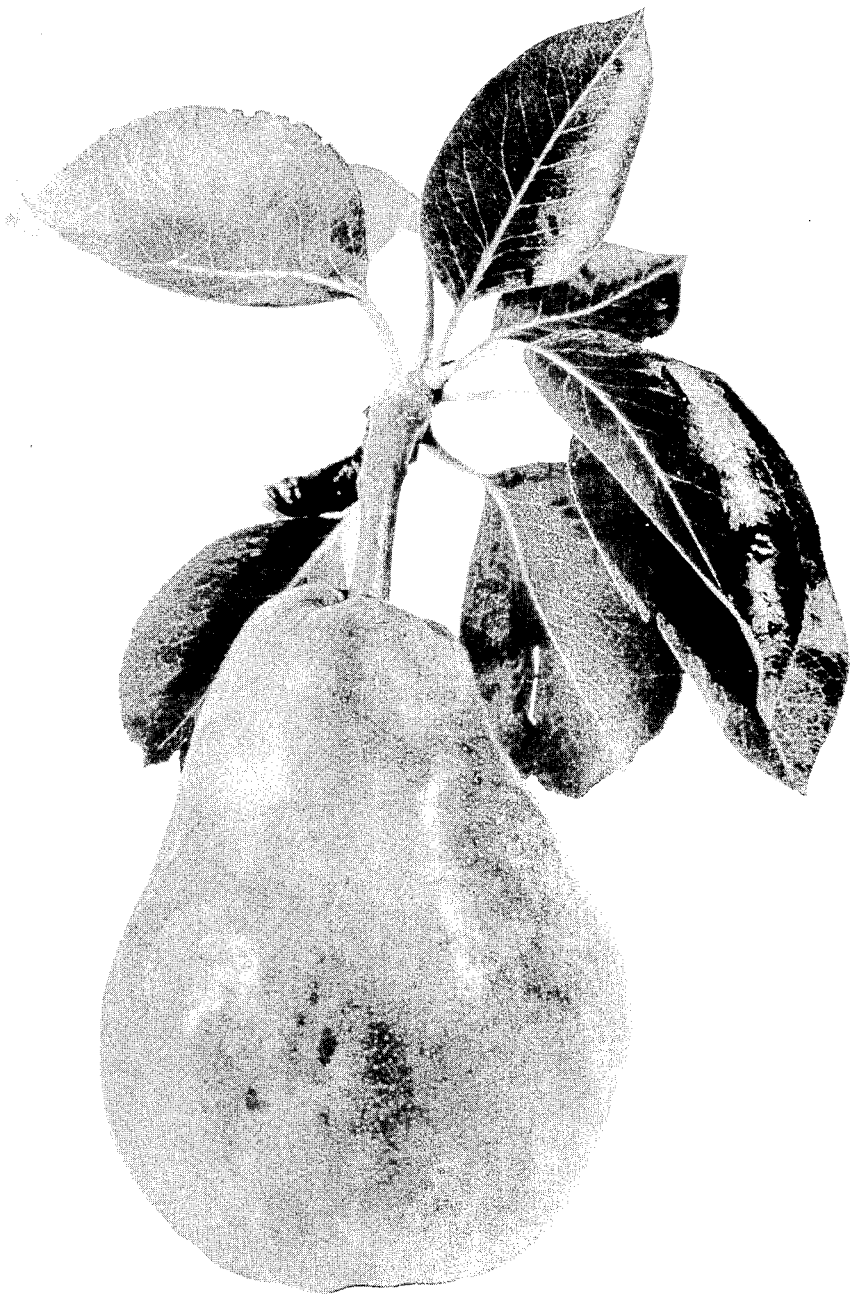
Inventor
Walter H. Eller
By Robert Cobb
Attorneys Patented May 12, 1953 Plant Pat. 1,184

UNITED STATES PATENT OFFICE 1,184

PEAR TREE

Walter H. Eller, Yakima, Wash.

Application October 18, 1949, Serial No. 121,943

1 Claim. (Cl. 47—62)

The present discovery relates to a new and distinct variety of pear tree, originating as a limb sport from a "Bartlett" (unpatented) pear tree and having a number of important distinctions therefrom giving rise to a decided improvement in the fruit from a commercial standpoint. This new sport was discovered by me in my cultivated orchard in Yakima County, State of Washington.

Since this new variety most nearly resembles the parent variety, it is desirable to point out more particularly the dominating distinctive characteristics. In the first place, this new pear blossoms earlier and the blossoms are slightly larger than the known parent variety grown under comparable conditions. The tree is practically free from second blooms, and the foliage is larger and of darker green. Its spurs are larger and healthier, the spur growth being above the average, with light sucker growth.

The tree of this new variety is a heavy bearer, frost resistant and blight resistant, and the fruit texture is far superior to that of the parent variety and the cells are uniform.

Further notable characteristics of the fruit are the fact that its fruiting season is four or five weeks ahead of the "Bartlett" variety in the vicinity of Yakima, Washington, and the sugar content at the picking date is ideal as evidenced by the fact that in canning the fruit it was found to be unnecessary to use sugar, this indicating a relatively low acid content in the fruit. The fruit at picking time is uniformly large, grading No. 1, and has good keeping qualities; it hangs to spur until fully ripe, and picks easy at picking time which is three to four weeks earlier than the parent; the seed formation is uniform and the fruit shows a slight pink blush on the sun side.

Asexual reproduction of the new variety shows the foregoing characteristics come true to form and are established.

In the drawing is illustrated one of the specimens of the fruit as well as typical specimens of the foliage.

This new variety was asexually reproduced at Yakima, Washington, by budding.

The following is a detailed description of the new variety, reference to color being in accordance with ordinary dictionary significance:

Tree: Medium size; vigorous; spreading; rapid growing; hardy; productive; regular bearer.

*Trunk.*—Stocky; medium smooth.

*Branches.* — Medium slender; medium smooth; much branching; grey. Lenticels—medium number; medium size.

*Leaves.*—Length—3¼ inches; width 2¼ inches. Large; wide; long; ovate; abruptly pointed; thick; medium green; smooth. Margin—crenate; finely serrate. Petiole—medium length, ¾ inch; medium slender.

*Flowers.*—Date of bloom—April 14th. Early compared with other varieties; medium size; white.

Fruit: Maturity when described—July 24th, eating hard.

*Size.*—Uniform. Axial diameter—4 inches. Transverse—2⅞ inches.

*Form.* — Ovoid. Cavity — symmetrical; rounded; flaring toward apex; furrowed; pubescent toward apex. Depth—⅛ inch; breadth—1 inch. Basin—unsymmetrical; rounded; base wide; furrowed; pubescent. Depth ¼ inch; breadth ¼ inch. Stem—stout; pubescent. Length — ¾ inch; breadth—$\frac{3}{16}$ inch. Calyx—open; segments persistent; broadly lanceolate; acute. Length—⅛ inch. Converged from base. Eye—medium size.

*Skin.*—Thin; smooth; glossy; waxed. Dots—conspicuous; many; small; even; submerged; circular. Color of dots—dark green. Distribution of dots—general. Ground color—light green. Color markings— blushed, light pink blush. Bloom—abundant. Scarfskin—gray. Distribution—even. General color effect—medium green with light pink blush.

Flesh: Juicy.

*Color of flesh.*—White with yellowish tint.

*Texture.*—Firm.

*Flavor.*—Sweet; rich aroma.

*Quality.*—Good.

Core: Median.

*Bundle area (longitudinal section).*—Medium size; oblate; symmetrical.

*Halves of area.*—Unequal.

*Bundles.*—Reddish tinge; inconspicuous.

*Core lines.*—Clasping.

Seeds: Number perfect—11; imperfect—2. Number in one cell—3 at most.

*Length.*—¼ inch.

*Breadth.*—⅛ inch.

*Color.*—Brown.

Use: Market; culinary.

Keeping quality: Good. Number of days in cold storage at an average temperature of approximately 40 to 42 degrees—127 days.

Resistance to:

*Insects.*—Good resistance to aphis, as evidenced by comparison with heavily infested "Bartlett" trees grown in the same orchard under comparable conditions, without any damaging effects upon my new variety.

*Disease.*—Good resistance to mildew, as evidenced by comparison with mildew-infected "Bartlett" trees grown in the same orchard under comparable conditions, without any damage to my new variety; also excellent resistance to "pear blight," as evidenced by deliberate inoculation of trees of my new variety with fungus growth of pear blight from other varieties, yet the trees of my new variety did not become infected and remained immune.

I claim:

A new and distinct variety of pear tree, characterized as to novelty by its early blooming season, large healthy spur growth and light sucker growth; by its early and heavy bearing habit, resistant to frost and blight; by the excellent texture of the fruit and by the superior qualities of the fruit for storage, canning and eating purposes, substantially as shown and described.

WALTER H. ELLER.

References Cited in the file of this patent

UNITED STATES PATENTS

| Number | Name | Date |
|---|---|---|
| Pl. Pt. 1,095 | Kalle | May 13, 1952 |